United States Patent
Choi et al.

(10) Patent No.: US 6,958,143 B2
(45) Date of Patent: Oct. 25, 2005

(54) CHEWING GUM COMPOSITION FOR EFFECTIVELY ELIMINATING NICOTINE ACCUMULATED IN A HUMAN BODY

(75) Inventors: Jin Hwan Choi, Seoul (KR); Hoe Jin Roh, Seoul (KR); Ki Jeong Lee, Gyeonggi-do (KR); Cheon Ho Park, Gyeonggi-do (KR); Chan Su Rha, Seoul (KR)

(73) Assignee: Tongyang Confectionery Co., Seoul (KR)

( * ) Notice: Subject to any disclaimer, the term of this patent is extended or adjusted under 35 U.S.C. 154(b) by 292 days.

(21) Appl. No.: 10/224,450

(22) Filed: Aug. 21, 2002

(65) Prior Publication Data

US 2003/0129145 A1 Jul. 10, 2003

(30) Foreign Application Priority Data

Jan. 10, 2002 (KR) .......................................... 2002-1327

(51) Int. Cl.[7] .............................. A61K 9/68; A23G 3/30
(52) U.S. Cl. ........................... 424/48; 424/58; 424/440; 424/439; 426/3; 426/4; 426/5; 426/548
(58) Field of Search ............................. 424/48, 440, 58, 424/439; 426/3, 4, 5, 548

(56) References Cited

U.S. PATENT DOCUMENTS

| 4,415,593 | A | * | 11/1983 | Glass et al. ..................... 426/4 |
|---|---|---|---|---|
| 4,906,480 | A | * | 3/1990 | Kashket .......................... 426/3 |
| 5,128,155 | A | * | 7/1992 | Song et al. ..................... 426/5 |
| 5,679,389 | A | * | 10/1997 | Wong et al. .................... 426/3 |
| 6,248,346 | B1 | * | 6/2001 | Hara et al. ................... 424/440 |
| 6,592,849 | B2 | * | 7/2003 | Robinson et al. ............. 424/48 |

FOREIGN PATENT DOCUMENTS

| KR | 1993-0003817 | 5/1993 |
|---|---|---|
| KR | 1994-0002648 | 3/1994 |
| KR | 0158756 | 8/1998 |
| KR | 10-0233325 | 9/1999 |
| KR | 10-0249357 | 12/1999 |

* cited by examiner

*Primary Examiner*—Gary Kunz
*Assistant Examiner*—Mina Haghighatian
(74) *Attorney, Agent, or Firm*—Buchanan Ingersoll PC

(57) ABSTRACT

Disclosed is a chewing gum composition capable of eliminating nicotine component from the body of a person chewing the chewing gum. Such a chewing gum composition functions to convert the nicotine produced in a human body after smoking to cotinine and to discharge the cotinine into urine. Accordingly, by chewing the chewing gum of the present invention, not only nicotine can be eliminated from the body, but also the incidence of cancer due to nicotine can be largely reduced.

11 Claims, No Drawings

CHEWING GUM COMPOSITION FOR EFFECTIVELY ELIMINATING NICOTINE ACCUMULATED IN A HUMAN BODY

FIELD OF THE INVENTION

The present invention relates to a chewing gum composition for eliminating nicotine, and more particularly to such a composition capable of eliminating the nicotine component from the body of a person chewing the chewing gum.

DESCRIPTION OF THE PRIOR ART

Nicotine is known as a toxic material contained in large quantities in tobacco, which stimulates or paralyzes the central nervous system and peripheral nerves and contracts blood vessels. In particular, N-nitrosamine, a metabolic product of nicotine is known as a strong carcinogen (Eugene et al., *Carcinogenesis*, 20: 133–137, 1999) and carcinogenic activities have been reported in about 200 kinds of N-nitrosamines until recently.

Besides N-nitrosamine, cotinine, another metabolic product of nicotine, and keto acid and hydroxy acid, other metabolic products of nicotine can act as competitive inhibitors which disturb the conversion path of nicotine to carcinogenic N-nitrosamine by aid of cytochrome $P_{450}$, an enzyme existing in the liver and the like. If, therefore, the conversion path of nicotine to cotinine can be activated so as to increase the production of cotinine and simultaneously an activity of enzyme participating in the production of nitrosamine can be inhibited, nicotine accumulated in a human body by smoking can be effectively eliminated and thus cancer due to nicotine will be prevented.

Quercetin, EGCG (epigallocatechin gallate), catechin and so forth have been reported as materials capable of eliminating such nicotine, but there have never been cases of producing foods, especially chewing gums using these materials.

Meanwhile, natural substances separated from plants or fruits have been used for the purpose of disease treatment since several thousands years ago. In particular, many kinds of herb medicines have been utilized for treatment of patients in the Orient for a long time, but active compositions or physiologic mechanism of action of them have never been scientifically studied.

It is known that, for those who always ingest fresh fruit and vegetables, there is a little probability of getting cancer such as heart diseases, lung cancer, esophagus cancer, larynx cancer and so forth, and this is attributable to the fact that unique compositions contained in the foods which they ingest have antioxidant actions and competitive inhibition actions against specific carcinogenic enzymes

DISCLOSURE OF THE INVENTION

The inventors have reached completion of the present invention by developing a chewing gum containing materials with nicotine-eliminating activities on the way of studying methods for effectively eliminating nicotine accumulated in a human body due to smoking, reducing production of carcinogens, and aiding people to succeed in abstention from smoking by minimizing the intensity and the period of abstinence symptoms appearing when they quit smoking.

Accordingly, an object of the present invention is to provide a chewing gum composition for eliminating nicotine, which exhibits a function of converting nicotine produced in a human body due to smoking to cotinine and discharging it into urine.

To achieve this object, the present invention provides a chewing gum composition comprising 0.01 to 10% by weight of material with nicotine-eliminating activity; 50 to 89% by weight of saccharide; and 10 to 40% by weight of chewing gum base, all based on the total weight of the composition.

BEST MODE FOR CARRYING OUT THE INVENTION

The chewing gum composition of the present invention can be preferably produced in such a way that saccharide syrup is further added to the composition in an amount of 0.01 to 20% by weight.

The chewing gum composition of the present invention may also be produced in a manner that at least one agent selected from the group consisting of flavor, stabilizer, pigment, emulsifier, and brightener is further added to the composition.

Now, the chewing gum composition in accordance with the present invention will be described in detail.

The chewing gum composition of the present invention is characterized in that it comprises 0.01 to 10% by weight of material with nicotine-eliminating activity, 50 to 89% by weight of saccharide and 10 to 40% by weight of chewing gum base, all based on the total weight of the composition.

Although quercetin, EGCG (epigallocatechin gallate) or catechin, all of which are well-known as materials with nicotine-inhibiting activity in the art, is generally used as the material with nicotine-eliminating activity, it is preferred to use a extract of mixture of green tea, mulberry leaf, gingko nut, licorice, dried orange peel, apple, lemon and celery (hereinafter referred to as "extract of 8-species mixture").

The extract of 8-species mixture can be separated by crushing apple, lemon and celery, squeezing out their juices, putting green tea, mulberry leaf, gingko nut, licorice and dried orange peel into a liquid mixture of the juices, and extracting a extract of mixture from the liquid mixture at a temperature of 50 to 150° C., preferably 100° C. for 1 to 8 hours, preferably for 4 hours an filtering the extract.

The nicotine-eliminating material is preferably added to the chewing gum composition of the present invention in an amount of 0.01 to 10% by weight and is more preferably added to the composition in an amount of 1% by weight.

The saccharide such as sugar, glucose, isomalt or xylitol is added to the chewing gum composition of the present invention so as to have a sweet taste. In order to have a suitable sweet taste, the saccharide is preferably added to the composition in an amount of 50 to 89% by weight and is more preferably added to the composition in an amount of 65% by weight.

The chewing gum base is preferably added to the chewing gum composition of the present invention in an amount of 10 to 40% by weight and is more preferably added to the composition in an amount of 25% by weight. This content range of the chewing gum base is preferred because problems of poor conglomeration, cleavage and fracture in forming the chewing gum may arise if the chewing gum base is added to the composition in an amount of below 10% by weight and texture feel of the chewing gum is too tough if the chewing gum base is added to the composition in an amount of above 40% by weight.

Saccharide syrup can be further added to the chewing gum composition of the present invention in order to soften physical properties of the chewing gum and cause the chewing gum to be conglomerated well. Preferably, the saccharide syrup used in the composition is selected from the group consisting of sortitol 80, starch syrup, maltitol syrup and sorbitol syrup, and is more preferably added to the composition in an amount of 0.01 to 20% by weight.

Also, the chewing gum composition of the present invention may be produced in a manner that, in addition to the saccharide syrup, at least one agent selected from the group consisting of flavor, stabilizer, pigment, emulsifier, and brightener is further added to the composition.

Flavor is added to the composition in order to make the smell of the chewing gum appealing and any one selected from the group consisting of mint flavor, fruit flavor and herb flavor can be used, but the present invention is not limited thereto. The flavor is preferably added to the composition in an amount of less than 5% by weight because a problem of excessive intense perfume may arise if the flavor is added to the composition in an amount of above 5% by weight.

In addition, stabilizer such as gum arabic, gelatin or konjac carrageenan can be added to the chewing gum composition of the present invention. The stabilizer, which is also called as a thickening agent, is material helpful in not only increasing stickiness and emulsification stability of food, but also preserving freshness and form of food from changes during processing heating or storage. Also, it is usually added in order to enhance the eating feel or touch feel. In the present invention, the stabilizer is preferably added to the composition in an amount of less than 10% by weight because the stabilizer in an amount of above 10% by weight may give rise to a nasty smell and bad taste problems.

Additionally, natural pigment such as gardenia blue color, gardenia yellow color, caramel color or grape skin extract color or artificial coloring agent can be further added to the chewing gum composition of the present invention for visual effect. Note that the kind of the added pigment or coloring agent is not limited thereto and the pigment or coloring agent is preferably added to the composition in an amount of less than 5% by weight.

Emulsifier such as sucrose esters of fatty acid or lecithin can be also added to the chewing gum composition of the present invention. The emulsifier is generally added so as to evenly disperse the flavor in a sugar solution at the production of chewing gum and is preferably added to the composition in an amount of less than 10% by weight. This content range of the emulsifier is preferred because a nasty smell or bad taste problems may arise if the emulsifier is added in an amount above 10% by weight.

Moreover, brightener such as carnauba wax or shellac can be further added to the chewing gum composition of the present invention. The brightener, having an intention of adding brightness to the chewing gum and thus giving visual superiority to the final produced chewing gum, is preferably added to the composition in an amount of less than 2% by weight.

Hereinafter, preferred embodiments of the present invention will be described in detail. Herein, it should be noted that the following embodiments are illustrated only by way of example and the present invention is not limited thereto.

PRODUCTION EXAMPLE 1

Production of Chewing Gum Containing Extract of 8-Species Mixture (Case 1)

1-1. Production of Extract of 8-species Mixture

After celery, apple and lemon were washed twice with distilled water, they were crushed using a wet crusher. The mixture solution was produced by adding 10 times of distilled water to the crushed substances, squeezing juices from the crushed substances and the distilled water, separating the dregs from the juices, and then filtering the squeezed juices with a 100-mesh sieve.

Thereinafter, green tea, mulberry leaf, licorice, gingko nut and dried orange peel were put into the mixture solution, 20 times of distilled water was applied to the mixture solution, and then the resultant mixture solution was extracted at a temperature of 100° C. for 4 hours. The extracted solution was filtered with a 100-mesh sieve, was filtered again with a 1 $\mu$m-housing filter, and was filtered once more with diatomaceous earth so as to be concentrated.

1-2. Production of Chewing Gum Containing Extract of 8-species Mixture

Chewing gum containing the extract of 8-species mixture obtained from the above Production Example 1-1 was produced.

For the production of the chewing gum, chewing gum base was heated at a temperature of 40° C., xylitol (Bolak Co., Ltd.) and isomalt (Palatinit Company) were added to the chewing gum base, and then the extract of 8-species mixture, produced in the above Production Example 1-1, was put into and sufficiently mixed with the chewing gum base. The chewing gum was finally produced by forming the mixture with a forming machine (Young-Jin Ind.) while spraying the isomalt and then by ripening the formed mixture for 2 days.

PRODUCTION EXAMPLE 2

Production of Chewing Gum Containing Extract of 8-species Mixture (Case 2)

Using a compounding ratio of raw materials listed in below in Table 1, including the extract of 8-species mixture obtained from the above Production Example 1-1, chewing gum was produced.

First, chewing gum base was heated at a temperature of 40° C. and then sortitol 80 (Paik-Kwang Ind.) was admixed with the chewing gum base. After xylitol, isomalt and mint flavor as flavor were added thereto, the extract of 8-species mixture produced in the above Production Example 1-1 was put into and sufficiently mixed with the chewing gum base. The resultant mixture was formed with a forming machine while being sprayed with the isomalt and then was ripened for 2 days. After ripening, the formed gum was coated with a mixture solution of isomalt and gelatin. During the coating, sucrose esters of fatty acid as emulsifier was put into and mint flavor was added to the coating solution so as to aromatize the coated layer. The chewing gum was finally produced by coloring the coated gum with gardenia blue color and treating the colored gum with carnauba wax to give brightness.

TABLE 1

| Compounding ratio in Production Example 2 | |
|---|---|
| Name of raw material | Compounding ratio (wt. %) |
| Extract of 8-species mixture | 1 |
| Chewing gum base | 25 |
| Sortitol 80 | 5.98 |
| Isomalt | 35.0 |
| Xylitol | 30.0 |

TABLE 1-continued

Compounding ratio in Production Example 2

| Name of raw material | Compounding ratio (wt. %) |
|---|---|
| Mint flavor | 1.5 |
| Gelatin | 1 |
| Gardenia blue color | 0.5 |
| Sucrose esters of fatty acid | 0.01 |
| Carnauba wax | 0.01 |
| Total | 100 |

PRODUCTION EXAMPLE 3

Production of Chewing Gum Containing Quercetin

Using a compounding ratio of raw materials listed below in Table 2, including quercetin (Sigma, USA), chewing gum was produced.

TABLE 2

Compounding ratio in Production Example 3

| Name of raw material | Compounding ratio (wt. %) |
|---|---|
| Quercetin | 0.1 |
| Chewing gum base | 25 |
| Sortitol 80 | 6.88 |
| Isomalt | 35.0 |
| Xylitol | 30.0 |
| Mint flavor | 1.5 |
| Gelatin | 1 |
| Gardenia blue color | 0.5 |
| Sucrose esters of fatty acid | 0.01 |
| Carnauba wax | 0.01 |
| Total | 100 |

PRODUCTION EXAMPLE 4

Production of Chewing Gum Containing Catechin

Using a compounding ratio of raw materials listed below in Table 3, including catechin (Sigma, USA), chewing gum was produced.

TABLE 3

Compounding ratio in Production Example 4

| Name of raw material | Compounding ratio (wt. %) |
|---|---|
| Catechin | 0.1 |
| Chewing gum base | 25 |
| Sortitol 80 | 6.88 |
| Isomalt | 35.0 |
| Xylitol | 30.0 |
| Mint flavor | 1.5 |
| Gelatin | 1 |
| Gardenia blue color | 0.5 |
| Sucrose esters of fatty acid | 0.01 |
| Carnauba wax | 0.01 |
| Total | 100 |

PRODUCTION EXAMPLE 5

Production of Chewing Gum Containing EGCG (Epigallo-catechin Gallate)

Using a compounding ratio of raw materials listed below in Table 4, including EGCG (Sigma, USA), chewing gum was produced.

TABLE 4

Compounding ratio in Production Example 5

| Name of raw material | Compounding ratio (wt. %) |
|---|---|
| EGCG | 0.1 |
| Chewing gum base | 25 |
| Sortitol 80 | 6.88 |
| Isomalt | 35.0 |
| Xylitol | 30.0 |
| Mint flavor | 1.5 |
| Gelatin | 1 |
| Gardenia blue color | 0.5 |
| Sucrose esters of fatty acid | 0.01 |
| Carnauba wax | 0.01 |
| Total | 100 |

EXAMPLE 1

Verification on Nicotine Decomposition Effect of Chewing Gum

In order to verify nicotine decomposition effect of the chewing gum produced in Production Example 1–2), clinical trials were performed for thirty-six robust male persons in their twenties to thirties, who have smoked cigarettes available in the market for two years or more. Control groups (a first group of sixteen persons and a second group of sixteen persons), chewing general chewing gums, were subjected to the clinical trial on one day and test groups (a first group of sixteen persons and a second group of sixteen persons), chewing the chewing gum containing the extract of 8-species mixture produced in Production Example 1-2), were subjected to the clinical trial on another day, but all the trials progressed during the same time period of each day, that is, at from 10 a.m. to 6 p.m. In this case, the thirty-six persons of the control groups were the same people as the thirty-six persons of the test groups.

The thirty-six persons to be subjected to the clinical trials were cautioned neither to drink nor overwork on the day before the test and thus they were caused to constantly maintain their body condition. The clinical trials were conducted in a manner listed below in Tables 5 and 6, and the persons belonging to the first group were caused to chew one piece of chewing gum and the persons belonging to the second group were caused to chew three pieces of chewing gum.

TABLE 5

Clinical trial for control groups

| Time | Details of test |
|---|---|
| 10:00 | Smoking a piece of cigarette, chewing a piece (three pieces) of general chewing gum after ingesting 200 ml of water |
| 10:30 | Spitting out gum having been chewed, chewing a piece (three pieces) of general gum |
| 10:50 | Primary urine gathering |
| 11:00 | Smoking a piece of cigarette, chewing a piece (three pieces) of general chewing gum after ingesting 200 ml of water |
| 11:30 | Spitting out gum having been chewed, chewing a piece (three pieces) of general gum |
| 11:50 | Secondary urine gathering |
| 12:00 | Smoking a piece of cigarette, chewing a piece (three pieces) of general gum |
| 12:50 | Lunch time (Chewing apiece (three pieces) of general gum after lunching and ingesting 200 ml of water) |

TABLE 5-continued

Clinical trial for control groups

| Time | Details of test |
|---|---|
| 12:50 | Third time urine gathering |
| 13:00 | Smoking a piece of cigarette, chewing a piece (three pieces) of general chewing gum after ingesting 200 ml of water |
| 14:00 | Smoking a piece of cigarette, chewing a piece (three pieces) of general gum |
| 14:50 | Fourth time urine gathering |
| 15:00 | Smoking a piece of cigarette, chewing a piece (three pieces) of general chewing gum after ingesting 200 ml of water |
| 16:00 | Smoking a piece of cigarette, chewing a piece (three pieces) of general gum |
| 17:00 | Smoking a piece of cigarette, chewing a piece (three pieces) of general gum |
| 18:00 | Fifth time urine gathering |

TABLE 6

Clinical trial for test groups

| Time | Details of test |
|---|---|
| 10:00 | Smoking a piece of cigarette, chewing a piece (three pieces) of chewing gum of the present invention after ingesting 200 ml of water |
| 10:30 | Spitting out gum having been chewed, chewing a piece (three pieces) of gum of the present invention |
| 10:50 | Primary urine gathering |
| 11:00 | Smoking a piece of cigarette, chewing a piece (three pieces) of chewing gum of the present invention after ingesting 200 ml of water |
| 11:30 | Spitting out gum having been chewed, chewing a piece (three pieces) of gum of the present invention |
| 11:50 | Secondary urine gathering |
| 12:00 | Smoking a piece of cigarette, chewing a piece (three pieces) of gum of the present invention |
| 12:50 | Lunch time (Chewing a piece (three pieces) of gum of the present invention alter lunching and ingesting 200 ml of water) |
| 12:50 | Third time urine gathering |
| 13:00 | Smoking a piece of cigarette, chewing a piece (three pieces) of chewing gum of the present invention after ingesting 200 ml of water |
| 14:00 | Smoking a piece of cigarette, chewing a piece (three pieces) of gum of the present invention |
| 14:50 | Fourth time urine gathering |
| 15:00 | Smoking a piece of cigarette, chewing a piece (three pieces) of chewing gum of the present invention after ingesting 200 ml of water |
| 16:00 | Smoking a piece of cigarette, chewing a piece (three pieces) of gum of the present invention |
| 17:00 | Smoking a piece of cigarette, chewing a piece (three pieces) of gum of the present invention |
| 18:00 | Fifth time urine gathering |

Urines gathered from the tests were immediately stored at a temperature of 20° C. below zero and were taken out after 48 hours to be subjected to quantitative analyses for the quantity of cotinine, major metabolic product of nicotine in the urine, using DBA assay (Robert et al., *Clin. Chim. Acta.* 165: 45–52, 1987).

All the tests for the quantitative analyses were conducted twice, respectively so as to enhance the reliability of the test. The tests progresses as follows:

500 $\mu$l of each urine or a standard solution was put into a 1.5 ml-test tube, and 250 $\mu$l of a 4M sodium acetate buffer solution (pH 4.7), 100 $\mu$l of 1.5 M KCN, 100 $\mu$l of 0.4 M chloroamine-T and 500 $\mu$l of 78 mM barbituric acid in acetone/water (50/50, v/v) were added in sequence to each test tube and were sufficiently mixed with the urine or standard solution for 10 seconds. The resultant mixture were reacted at a room temperature (22° C.) and 100 rpm for 15 minutes and terminated the reaction by adding 100 $\mu$l of 1 M sodium metabisulfite to the mixture. Cotinine was quantified by measuring absorbance of the reacted solution at a wavelength of 490 nm and comparing it with that of the cotinine standard solution and the results of quantification are listed below in table 7.

TABLE 7

Results of cotinine quantification

| | Average of cotinine (M) | | | | Increase rate of cotinine (%) | |
|---|---|---|---|---|---|---|
| | Control groups | | Test groups | | | |
| | First group | Second group | First group | Second group | First group | Second group |
| Primary | 39.578 | 28.961 | 51.422 | 41.978 | 29.92572 | 44.94665 |
| Secondary | 29.049 | 16.735 | 33.725 | 29.636 | 16.09694 | 77.08993 |
| Third time | 35.106 | 21.731 | 34.462 | 29.427 | −1.83444 | 35.41485 |
| Fourth time | 38.367 | 23.729 | 50.45 | 37.167 | 31.49321 | 56.63113 |
| Fifth time | 21.854 | 16.657 | 26.854 | 28.961 | 22.87911 | 73.86684 |

From Table 7 showing the cotinine concentrations in the urines of the entire groups, it can be confirmed that the cotinine concentration in urine is increased in the groups chewing the chewing gum of the present invention by 30 to 80% than in the groups chewing general gum. Also, compared with the first group who chewed one piece of the gum of the present invention per time and chewed a total of ten times a day, the second group who chewed three pieces of the gum of the present invention per time exhibited an increase rate of cotinine larger by two or three times than that of the first group. Accordingly, it can be also confirmed that the increase rate of cotinine in the urine grows larger as the amount of the chewing gum of the present invention is increased.

That is, this test results lead us to the conclusion that, by chewing the chewing gum of the present invention, nicotine accumulated in a body due to smoking is converted to cotinine and is discharged into urine, which results in eliminating nicotine from a body of a person chewing the gum.

EXAMPLE 2

Sensory Test

For the thirty-six persons having been appointed as clinical subjects in Example 1, sensory tests of the chewing gum produced in Production Example 2 were performed. The result thereof is listed below in Table 8.

TABLE 8

Result of sensory tests

| Item | Poor | Ordinary | Good | Excellent |
|---|---|---|---|---|
| Taste | 2 | 22 | 11 | |
| Chewing feel | 2 | 22 | 9 | 3 |
| Size | 1 | 13 | 17 | 5 |

As shown in Table 8, a high value was set on the chewing gum produced in accordance with the present invention in aspect of its taste, chewing feel and size. Also, upon investigation whether a smoking desire is lowered or not for clinical subjects taking the chewing gum of the present invention, twenty-five persons confirmed a lowering in smoking desire. The chewing gum of the present invention, therefore, can be used as a supporting agent for quitting smoking.

INDUSTRIAL APPLICABILITY

As described above, the present invention provides a chewing gum composition capable of eliminating nicotine. Such a chewing gum composition functions to convert nicotine produced in a human body after smoking to cotinine and to discharge the cotinine into urine. Accordingly, by chewing the chewing gum of the present invention, not only nicotine can be eliminated from the body, but also the incidence of cancer due to nicotine can be largely reduced.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A chewing gum composition for effectively eliminating nicotine accumulated in a human body, comprising:
    (a) 0.01 to 10% by weight of material with nicotine-eliminating activity which is an extract of a mixture composed of green tea, mulberry leaf, gingko nut, licorice, dried orange peel, apple, lemon and celery;
    (b) 50 to 89% by weight of saccharide; and
    (c) 10 to 40% by weight of chewing gum base, all based on the total weight of the composition.

2. The chewing gum composition according to claim 1, wherein the saccharide is sugar, glucose, isomalt or xylitol.

3. The chewing gum composition according to claim 1, wherein saccharide syrup is further added to the composition in a content of 0.01 to 20% by weight.

4. The chewing gum composition according to claim 3, wherein the saccharide syrup is selected from the group consisting of sortitol 80, starch syrup, maltitol syrup and sorbitol syrup.

5. The chewing gum composition according to claim 1, wherein at least one agent selected from the group consisting of flavor, stabilizer, pigment, emulsifier, and brightener is further added to the composition.

6. The chewing gum composition according to claim 5, wherein the flavor is selected from the group consisting of mint flavor, fruit flavor and herb flavor.

7. The chewing gum composition according to claim 5, wherein the stabilizer is selected from the group consisting of gum Arabic, gelatin and konjac carrageenan.

8. The chewing gum composition according to claim 5, wherein the pigment is natural pigment or artificial coloring agent.

9. The chewing gum composition according to claim 8, wherein the natural pigment is selected from the group consisting of gardenia blue color, gardenia yellow color, caramel color and grape skin extract color.

10. The chewing gum composition according to claim 5, wherein the emulsifier is sucrose ester of fatty acid or lecithin.

11. The chewing gum composition according to claim 5, wherein the brightener is carnauba wax or shellac.

* * * * *